(12) United States Patent
Waldöfner et al.

(10) Patent No.: US 9,408,912 B2
(45) Date of Patent: Aug. 9, 2016

(54) AGGLOMERATING MAGNETIC ALKOXYSILANE-COATED NANOPARTICLES

(75) Inventors: Norbert Waldöfner, Duisburg (DE); Andreas Jordan, Berlin (DE)

(73) Assignee: MagForce AG, Berlin (DE)

( * ) Notice: Subject to any disclaimer, the term of this patent is extended or adjusted under 35 U.S.C. 154(b) by 0 days.

(21) Appl. No.: 13/877,891

(22) PCT Filed: Aug. 7, 2012

(86) PCT No.: PCT/EP2012/003381
§ 371 (c)(1),
(2), (4) Date: Jun. 26, 2013

(87) PCT Pub. No.: WO2013/020701
PCT Pub. Date: Feb. 14, 2013

(65) Prior Publication Data
US 2014/0154324 A1    Jun. 5, 2014

Related U.S. Application Data

(60) Provisional application No. 61/522,217, filed on Aug. 10, 2011.

(51) Int. Cl.
*A61K 41/00* (2006.01)
*H01F 1/00* (2006.01)
*A61K 9/51* (2006.01)

(52) U.S. Cl.
CPC ........... *A61K 41/0052* (2013.01); *A61K 9/5146* (2013.01); *H01F 1/0054* (2013.01)

(58) Field of Classification Search
CPC ...... H01F 1/0054; B82Y 40/00; B82Y 30/00; A61K 41/0052
See application file for complete search history.

(56) References Cited

U.S. PATENT DOCUMENTS

| | | | |
|---|---|---|---|
| 3,945,945 A | 3/1976 | Kiovsky et al. | |
| 4,169,912 A | 10/1979 | Schönafinger et al. | |
| 4,271,234 A | 6/1981 | Schönafinger et al. | |
| 4,744,802 A | 5/1988 | Schwabel | |
| 5,034,145 A | 7/1991 | Leising et al. | |
| 5,460,831 A | 10/1995 | Kossovsky et al. | |
| 5,462,751 A | 10/1995 | Kossovsky et al. | |
| 5,540,959 A | 7/1996 | Wang | |
| 5,547,748 A | 8/1996 | Ruoff et al. | |
| 5,593,781 A | 1/1997 | Nass et al. | |
| 5,616,311 A | 4/1997 | Yen | |
| 5,695,900 A * | 12/1997 | Selim | 430/106.2 |
| 5,718,907 A | 2/1998 | Labarre | |
| 5,916,539 A | 6/1999 | Pilgrimm | |
| 5,922,403 A | 7/1999 | Tecle | |
| 5,922,537 A | 7/1999 | Ewart et al. | |
| 5,928,958 A | 7/1999 | Pilgrimm | |
| 5,935,275 A | 8/1999 | Bugard et al. | |
| 6,022,500 A | 2/2000 | John et al. | |
| 6,045,821 A | 4/2000 | Garrity et al. | |
| 6,103,379 A | 8/2000 | Margel et al. | |
| 6,183,658 B1 | 2/2001 | Lesniak et al. | |
| 6,251,365 B1 | 6/2001 | Bauerlein et al. | |
| 6,541,039 B1 | 4/2003 | Lesniak et al. | |
| 6,548,264 B1 | 4/2003 | Tan et al. | |
| 6,638,494 B1 | 10/2003 | Pilgrimm | |
| 6,669,623 B1 | 12/2003 | Jordan | |
| 6,808,535 B1 | 10/2004 | Jordan | |
| 2004/0156846 A1 | 8/2004 | Daum et al. | |
| 2004/0265233 A1 * | 12/2004 | Holzer et al. | 424/9.32 |
| 2005/0090732 A1 | 4/2005 | Ivkov et al. | |
| 2005/0119725 A1 | 6/2005 | Wang et al. | |
| 2006/0211152 A1 | 9/2006 | Peng et al. | |
| 2006/0216239 A1 | 9/2006 | Zhang et al. | |
| 2006/0228554 A1 | 10/2006 | Tan et al. | |
| 2007/0090323 A1 | 4/2007 | Duguet et al. | |
| 2008/0081891 A1 | 4/2008 | Wang et al. | |
| 2008/0187595 A1 | 8/2008 | Jordan et al. | |
| 2008/0268061 A1 | 10/2008 | Jordan et al. | |

(Continued)

FOREIGN PATENT DOCUMENTS

| | | | |
|---|---|---|---|
| DE | 25 43 962 A1 | 4/1977 | |
| DE | 196 14 136 A1 | 10/1997 | |

(Continued)

OTHER PUBLICATIONS

Yamamura et al., J. Magnetism Magnetic Materials, 2004, 279, 210-217.*
Cole, A. J., et al. (2011). "Polyethylene glycol modified, cross-linked starch-coated iron oxide nanoparticles for enhanced magnetic tumor targeting." Biomaterials 32(8): 2183-93.
Del Campo, A. et al.; "Multifunctional Magnetite and Silica-Magnetite Nanoparticles: Synthesis, Surface Activation and Applications in Life Sciences", Journal of Magnetism and Magnetic Materials, Elsevier Science Publishers, Amsterdam, Nl, vol. 293, No. 1, 2005, pp. 33-40.
De Palma, R.; Silane Ligand Exchange to Make Hydrophobic Superparamagnetic Nanoparticles Water-Dispersible, American Chemical Society, Chem. Mater. 2007, vol. 19, pp. 1821-1831.
Feng, B. et al..: "Synthesis of $Fe_3O_4$/APTES/PEG diacid functionalized magnetic nanoparticles for MR imaging", Colloids and Surfaces. A: Physicochemical and Engineering Aspects, Elsevier, Amsterdam, NL, vol. 328, No. 1-3, 2008, pp. 52-59.

(Continued)

*Primary Examiner* — Kyle Purdy
(74) *Attorney, Agent, or Firm* — The Marbury Law Group, PLLC

(57) ABSTRACT

The present invention relates to a method for producing a suspension of agglomerates of magnetic alkoxysilane-coated metal nanoparticles, wherein an aqueous suspension of magnetic metal nanoparticles is incubated with alkoxysilane, wherein the incubation is carried out essentially in the absence of an organic solvent. The present invention further relates to suspension of agglomerates of magnetic alkoxysilane-coated metal containing nanoparticles obtainable by the method of the present invention and to a composition comprising agglomerates of magnetic alkoxysilane-coated metal nanoparticles, wherein the agglomerates have an average size of 30 to 450 nm, preferably of 50 to 350 nm and especially of 70 to 300 nm as determined by light scattering.

16 Claims, 3 Drawing Sheets

(56) References Cited

U.S. PATENT DOCUMENTS

Figure 1:
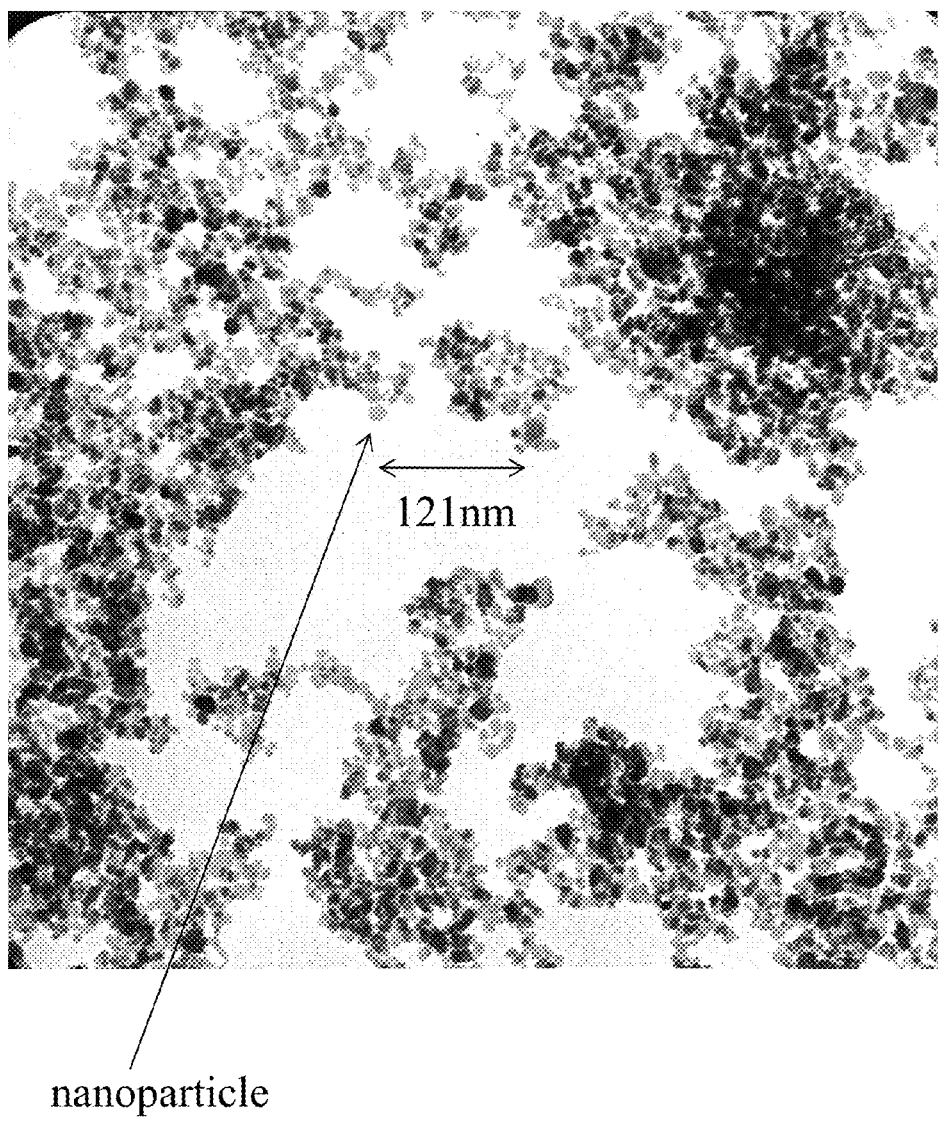

| | | |
|---|---|---|
| 2009/0060846 A1 | 3/2009 | Zhang et al. |
| 2009/0317327 A1 | 12/2009 | Pilgrimm |
| 2010/0104514 A1 | 4/2010 | Brougham et al. |
| 2010/0279118 A1 | 11/2010 | Hempenius |
| 2011/0052609 A1 | 3/2011 | Waldoefner et al. |
| 2011/0130616 A1 | 6/2011 | Seeney et al. |
| 2011/0223255 A1 | 9/2011 | Thiesen et al. |
| 2012/0107246 A1 | 5/2012 | Zhang et al. |
| 2012/0201760 A1 | 8/2012 | Tromsdorf et al. |
| 2012/0294806 A1 | 11/2012 | Chen et al. |
| 2013/0046274 A1 | 2/2013 | Zink et al. |
| 2013/0102545 A1 | 4/2013 | Gao et al. |

FOREIGN PATENT DOCUMENTS

| | | |
|---|---|---|
| DE | 102 61 406 A1 | 7/2004 |
| EP | 0 200 487 A2 | 5/1986 |
| EP | 0 472 990 B1 | 3/1992 |
| EP | 634991 | 1/1995 |
| EP | 0 667 148 A1 | 8/1995 |
| EP | 688834 | 12/1995 |
| EP | 689430 | 1/1996 |
| EP | 1648381 | 4/2006 |
| EP | 1945159 | 7/2008 |
| EP | 1952919 | 8/2008 |
| EP | 2247315 | 11/2010 |
| JP | 5-277355 A | 10/1993 |
| JP | 6-270155 A | 9/1994 |
| JP | 09-000646 | 1/1997 |
| WO | WO-88/00060 A1 | 1/1988 |
| WO | WO-90/01295 A1 | 2/1990 |
| WO | WO-90/03838 A1 | 4/1990 |
| WO | WO-93/24076 A1 | 12/1993 |
| WO | WO-96/02060 A1 | 1/1996 |
| WO | WO-98/40049 A2 | 9/1998 |
| WO | WO-98/58673 A1 | 12/1998 |
| WO | WO 00/56288 | 9/2000 |
| WO | WO 02/098364 | 12/2002 |
| WO | WO 2004/071370 | 8/2004 |
| WO | WO 2006/042724 | 4/2006 |
| WO | WO-2006/057533 A1 | 6/2006 |
| WO | WO-2006/108405 A2 | 10/2006 |
| WO | WO 2006/125452 | 11/2006 |
| WO | WO 2007/036682 | 4/2007 |
| WO | WO 2007/079276 | 7/2007 |
| WO | WO 2008/014623 | 2/2008 |
| WO | WO 2009/094568 | 7/2009 |
| WO | WO 2009/100716 | 8/2009 |
| WO | WO 2010/062615 | 6/2010 |
| WO | WO 2011/082796 | 7/2011 |
| WO | WO 2011/136654 | 11/2011 |
| WO | WO 2011/150212 | 12/2011 |
| WO | WO 2012/001579 | 1/2012 |
| WO | WO 2012/036978 | 3/2012 |

OTHER PUBLICATIONS

Guardia, P., et al. << Water-Soluble Iron Oxide Nanocubes with High Values of Specific Absorption Rate for Cancer Cell Hyperthermia Treatment >> (2012). ACS Nano 6(4): 3080-91.

Guardia, P., et al. << Heat rate influence on the systhesis of Iron Oxide nanoparticles : the case of Decanoic Acid >>,(2010), Chem Commun (Camb) 46(33): 6108-10.

Guardia, P., et al. "Controlled Sythesis of Iron Oxide Nanoparticles Over a Wide Size Range",(2010), Langmuir 26(8): 5843-7.

Gupta, A. K. et al., "Synthesis and surface engineering of iron oxide nanoparticles for biomedical applications," Biomaterials, (2005), vol. 26, 3995-4021.

Hermentin, P. et al., "Hinge-Thiol Coupling of Monoclonal Antibody to Silanized Iron Oxide Particles and Evaluation of Magnetic Cell Depletion," Bioconjugate Chem., (1990), vol. 1, No. 6, pp. 411-418.

Hyeon, T., et al. (2001). "Synthesis of Highly Crystalline and Monodisperse Maghemite Nanocrystallites without a Size-Selection Process." Journal ft he American Chemical Society 123(51): 12798-801.

Johannsen, M., et al. << Thermotherapy of Prostate Cancer Using Magnetic Nanoparticles : Feasibility, Imaging, and Three-Dimensional Temperture Distribution >>,(2007). Eur Urol. 52(6): 1653-61. Epub Nov. 17, 2006.

Jordan, A. et al., "Inductive heating of ferrimagnetic particles and magnetic fluids: physical evaluation of their potential for hyperthermia," International Journal of Hyperthermia, (1993), vol. 9, No. 1, pp. 51-68.

Jordan, A., et al. (1996). "Cellular uptake of magnetic fluid particles and their effects on human adenocarcinoma cells exposed to AC magnetic fields in vitro", Int J Hyperthermia. 12(6): 705-22.

Jordan, A., et al. (2006). "The effect of thermotherapy using magnetic nanoparticles on rat malignant glioma." J Neurooncol. 78(1): 7-14. Epub Nov. 29, 2005.

Jung, C. W. et al., "Physical and Chemical Properties of Superparamagnetic Iron Oxide MR Contrast Agents: Ferumoxides, Ferumoxtran, Ferumoxsil," (1995), Magnetic Resonance Imaging, vol. 13, No. 5, pp. 661-674.

Kim, D. K., et al. (2001). "Synthesis and characterization of surfactant-coated superparamagnetic monodispersed iron oxide nanoparticles." Journal of Magnetism and Magnetic Materials 225(1-2): 30-6.

Lesniak, C., et al. (1996). "Synthesis and Surface Modification of Deagglomerated Superparamagnetic Nanoparticles." MRS Proceedings 432: 169; Abstract.

Ma, Ming et al. << Preparation and Characterization of Magnetite Nanoparticles Caoted by Amino Silane >> , (2002) Elsevier Science, Colloids and Surfaces : Physicochem. Eng. Aspects 212, 219-26.

Maier-Hauff, K., et al. (2007). "Intracranial thermotherapy using magnetic nanoparticles combined with external beam radiotherapy: results of a feasibility study on patients with glioblastoma multiforme." J Neurooncol. 81(1): 53-60. Epub Jun. 14, 2006.

Maier-Hauff, K., et al. (2011). "Efficacy and safety of intratumoral thermotherapy using magnetic iron-oxide nanoparticles combined with external beam radiotherapy on patients with recurrent glioblastoma multiforme" J Neurooncol 103(2): 317-24 Epub Sep. 16, 2010.

Massart, R. (1981). "Preparation of Aqueous Magnetic Liquids in Alkaline and Acidic Medis" IEEE Trans. Magn. 17(2): 1247-48.

Mohapatra, M. and S. Anand (2010). "Synthesis and applications of nano-structured iron oxides/hydroxides—A review" , Int J of Engineering, Science and Technology. 2(8): 127-46.

Mohapatra, S. Et Al: "A simple synthesis of amine-derivatised superparamagnetic iron oxide nanoparticles for bioapplications", Journal of Materials Science, Kluwer Academic Publishers, BO, vol. 42, No. 17, 2007, pp. 7566-7574.

Moroz, P., et al. (2002). Magnetically mediated hyperthermia : current status and future directions >>, Int J Hyperthermia. 18(4): 267-84.

Park, J., et al. (2004). „Ultra-large-scale syntheses of monodisperse nanocrystals. Nat Mater 3(12): 891-5.

Pinkernelle, J., et al. (2005). "Imaging of single human carcinoma cells in vitro using a clinical whole-body magnetic resonance scanner at 3.0 T." Magn Reson Med 53(5): 1187-92.

Roque A C A et al: "Biocompatible and bioactive gum Arabic coated iron oxide magnetic nanoparticles", Journal of Biotechnology, Elsevier Science Publishers, Amsterdam, NL, vol. 144, No. 4, 2009, pp. 313-320.

Schnoor, A., et al. (2010). "Laserfragmentierung von anorganischen and organischen Mikropartikel-Suspensionen zu Nanopartikel-Kolloiden", Chemie Ingenieur Technik 82(3): 317-26.

Shen, X. C., et al. (2004). "Synthesis and characterization of 3-aminopropyltriethoxysilane-modified superparamagnetic magnetite nanoparticles." Chemistry Letters 33(11): 1468-9.

Smith, T. W. et al., "Colloidal Iron Dispersions Prepared via the Polymer-Catalyzed Decomposition of Iron Pentacarbonyl," J. Phys. Chem., (1980), vol. 84, 1621-1629.

Stelter, L., et al. (2010). "Modification of aminosilanized superparamagnetic nanoparticles: feasibility of multimodal detection using 3T MRI, small animal PET, and fluorescence imaging." Mol Imaging Biol 12(1): 25-34.

(56) References Cited

OTHER PUBLICATIONS

Steitz, B., et al. (2007). "Production and Biofunctionalization of Magnetic Nanobeads for Magnetic Separation of Messenger RNA." Biophysical Reviews and Letters 02(01): 109-22.

Sun, S. et al., "Monodisperse $MFe_2O_4$ (M=Fe, Co, Mn) Nanoparticles," J. Am. Chem. Soc., (2004) vol. 126, No. 1, pp. 273-279.

Thiesen, B. and A. Jordan (2008). "Clinical applications of magnetic nanoparticles for hyperthermia" Int J Hyperthermia. 24(6): 467-74.

Wang, L., et al. (2006). "One-pot synthesis and bioapplication of amine-functionalized magnetite nanoparticles and hollow nanospheres." Chem. Eur. J. 12(24): 6341-7.

Wang, Y. et al., ""Pulling" Nanoparticles into Water: Phase Transfer of Oleic Acid Stabilized Monodisperse Nanoparticles into Aqueous Solutions of $\alpha$-Cyclodextrin," Nano Letters, (2003), vol. 3, No. 11, pp. 1555-1559.

Yuan et al. (2004), "Surfactant mediated nanoparticle assembly of catalytic mesoporus crystalline iron oxide materials", Catalysis Today, 93-95: 743-750.

Zablotskaya, A. et al., "Synthesis and characterization of nanoparticles with an iron oxide magnetic core and a biologically active trialkylsilylated aliphatic alkanolamine shell," Journal of Magnetism and Magnetic Materials, (2007) vol. 311, pp. 135-139.

International Search Report and Written Opinion received in connection with international application No. PCT/EP2012/003381; dated Feb. 11, 2013.

International Preliminary Report on Patentability received in connection with international application No. PCT/EP2012/003381; dated Sep. 25, 2013.

* cited by examiner

AGGLOMERATING MAGNETIC ALKOXYSILANE-COATED NANOPARTICLES

Despite recent advances in tumor therapy of solid tumors such as antibodies, the need for more efficacious and cost-effective treatment options remains.

Thermotherapy or more specifically hyperthermia is an appealing approach for the treatment of cancer, as, compared to chemotherapy or radiation therapy, fewer side effects are expected for a wide range of tumor diseases due to its physical mode of action. However, currently available modalities are still suboptimal (Moroz et al. 2002) and warrant improvement.

One preferred modality of thermotherapy is a method wherein magnetic nanoparticles are directly introduced into a tumor. The nanoparticles are subsequently heated in an alternating magnetic field. Depending on the duration of treatment and the achieved intratumoral temperatures, the tumor cells are either directly destroyed (thermal ablation) or sensitized for concomitant chemo- or radiotherapy (hyperthermia). With this new procedure, it is possible to combat the tumor from inside out, thereby sparing surrounding healthy tissue. This treatment modality has shown promising therapeutic effects in the treatment of glioblastoma (Maier-Hauff et al. 2011).

Despite positive results from first clinical trials there is still room for improving the efficacy and/or reducing potential side effects or limitations of the therapy. One unsolved problem is that during instillation of the nanoparticles, deposits of the magnetic nanoparticles outside of target area occur in the surrounding tissue. Such external depots either cause unwanted side effects as they lead to increased temperatures outside of the target area upon heating in the alternating magnetic field, or they limit the applicable magnetic field strength used to heat the nanoparticle depots if such heating of surrounding tissue is avoided. This problem may be due to a high pressure within the injected tumor tissue which leads to an efflux of deposited nanoparticles during or immediately after injection. Furthermore, while nanoscale particles are required in order to have high specific absorption rates (SAR), such nanoparticles can easily travel within the interstitial space and thereby may get lost from the target tissue. Further, the amount of heat which can be 'deposited' within the tumor—by first depositing nanoparticles that are subsequently excited by the alternating magnetic field—is limited due to a suboptimal specific absorption rate (SAR) of the nanoparticles/the magnetic fluid which are used so far in the clinic.

Additionally, such nanoparticles need to be manufactured in a controlled fashion at large scale and reasonable cost, and need to be capable of being formulated in a stable formulation in order to become a marketable product.

The prior art describes a number of methods and uses of such nanoparticles, as reviewed by Gupta and Gupta (2005).

Lesniak et al. (1997) describe a process for the preparation of agglomerate-free nanoparticles. The process includes (i) preparing an aqueous suspension of ironoxide nanoparticles which partially form agglomerates, (ii) adding trialkoxysilanes and a water-miscible polar organic solvent, e.g. ethylene glycol, (iii) treating the resulting suspension with ultrasound in order to reduce agglomeration, (iv) removing the water by distillation under the action of ultrasound; and (v) removing remaining agglomerates. The process results in agglomerate-free nanoparticles with a hydrolysis-resistant coating based on alkoxysilanes. However, these nanoparticles, if applied locally to solid tumors, only partially remain at the site of injection probably due to their properties of being agglomerate-free. These nanoparticles get broadly distributed in the body thereby limiting both the remaining amount of nanoparticles within the target area as well increasing the risk of side effects due to accumulation of nanoparticles in surrounding tissues or elsewhere in the body. Furthermore, used ethylene glycol is very hard to get rid of due to its interaction with amino-groups of the alkoxysilane coating and its high boiling point (197° C.). Accordingly, the presence of ethylene glycol in the final product limits the applicability of the nanoparticles under safety and regulatory aspects.

Ruefenacht et al. (2006) disclose an injectable polymer-based formulation of heat-generating nanoparticles in a liquid carrier, which is able to form in-situ implants upon contact with a body fluid or tissue. Whereas this formulation seems to solve the problem of efflux of the nanoparticles from the tumor, the system preferably uses solvents such as N-methyl-2-pyrrolidone (NMP) or Dimethyl sulfoxide (DMSO). Both solvents are generally considered to have low toxicity and are frequently used for oral and transdermal formulations of drugs. However, little is known for the injection of the solvents into tissues or tumors, especially into the brain in case of brain tumors. Therefore, such solvents should be avoided. Furthermore, such formulations form upon injection a defined implant, whereas in the context of the present invention it is envisaged to achieve a certain distribution of the injected nanoparticles within the tumor/tissue, which is however confined to the tumor/tissue. Another disadvantage of this system is the anticipated volume increase within the tumor, if these injectable polymer-based formulations are injected into tumors, which may cause problems in certain tumor indications, especially in brain tumors, where space within the scull is limited. Together, such polymer-based formulations are not suited for the treatment of non-operable tumors.

The object of the present invention is, therefore, to provide improved biocompatible magnetic nanoparticles. In particular, the object of the present invention is to provide improved biocompatible magnetic nanoparticle for the treatment of tumors.

As shown in the examples, the inventors now have surprisingly found that the controlled aminosilanization of iron oxide nanoparticles in absence of organic solvents leads to magnetic nanoparticles with an incomplete condensation of the surface aminosilanes which results in a stable, water-based formulation of magnetic nanoparticles (magnetic fluids), which can be highly concentrated. Upon injection into tissue or tumor these magnetic fluids form favorable depots with a high retention rate within the target tissue. Accordingly, the inventors provide an improved method for manufacture, improved nanoparticles, and suitable suspensions and compositions (magnetic fluids) with an improved biocompatibility, improved depot formation within the target area and less side effects due to the absence of organic solvents and/or reduced efflux of deposited nanoparticles from the treatment area.

Consequently, the present invention provides biocompatible magnetic nanoparticles with a high specific absorption rate (SAR) which can be injected in the daily routine into tumor tissue, which remain at or near the injection site within the intended treatment area, e.g. the tumor, and do not substantially spread to surrounding tissue. Furthermore, the present invention provides a robust and cost-efficient manufacturing process for such biocompatible magnetic nanoparticles.

DEFINITIONS

"Specific Absorption Rate" (SAR) is a measure for the rate at which energy is absorbed by the nanoparticles upon exposure to the alternating magnetic field. It is dependent on the magnetic field strength and the frequency of the alternation of the polarization of the magnetic field. The SAR is preferably determined according to the method developed by Jordan et al. (1993) at a frequency of 100 kHz and a field strength of up to 18 kA/m, preferably at 3.5 kA/m and refers to the mass of used metal, e.g. iron (unit W/g metal).

"Zeta potential" refers to measured electrical potential of a colloidal nanoparticle in aqueous environment, measured with an instrument such as a Malvern ZetaSizer 3000 HSA at pH 5.2 and a conductivity of 2.0 mS/cm (each determined at 25° C.). The zeta potential describes the potential at the boundary between bulk solution and the region of hydrodynamic shear or diffuse layer.

In the context of the present invention, the term "about" means a deviation from the given number or value of ±10%, preferably of ±5% and especially of ±1%.

The term "magnetic" incorporates magnetic, paramagnetic, ferromagnetic, anti-ferromagnetic, ferrimagnetic, antiferrimagnetic and superparamagnetic. Preferably, nanoparticles according to this invention are paramagnetic, more preferably ferromagnetic, ferrimagnetic, antiferrimagnetic or superparamagnetic.

In a particularly preferred embodiment, the nanoparticles are superparamagnetic.

The term "nanoparticles" shall mean nanoparticles in the nanometer range, meaning nanoparticles from 1 to 100 nm with respect to its metal core as can be determined by electron microscopy. Preferably, the nanoparticles have a size of 5 to 25 nm, more preferably 7 to 20 nm and especially 9 to 15 nm.

"Metal nanoparticle" refers to magnetic nanoparticle, which contain metal or metal ions.

"Organic solvent" shall mean a liquid organic compound, i.e. a carbohydrate, with the power to dissolve solids, gases, or liquids. Examples of organic solvents according to the present invention, include, but are not limited to, ethylene glycol, acetone, toluol and equivalents.

The term "alkoxysilane coating" refers to a coating resulting from the polycondensation of alkoxysilanes, a process which is also referred to as "aminosilane coating". The term "polycondensation" as used herein generally means any condensation reaction of a monomer with two functional groups which leads to the formation of a polymer.

In a first aspect, the present invention relates to a method for producing a suspension of agglomerates of magnetic alkoxysilane-coated metal nanoparticles, wherein an aqueous suspension of magnetic metal nanoparticles is incubated with alkoxysilane, characterized in that said incubation is carried out essentially in the absence of an organic solvent.

In the context of the present invention, the term "incubating" or "incubation" means any experimental setup, experimental condition(s) or reaction mixture(s) which allow for the polycondensation of alkoxysilanes and thereby for the aminosilane coating of nanoparticles.

As shown in the examples, it has been found in the context of this invention that, for the treatment of tumors and other diseases, agglomerates of magnetic alkoxysilane-coated metal nanoparticles can better form deposits within the target area and fewer nanoparticles get lost into circulation or form deposits outside of the target area than magnetic alkoxysilane-coated metal nanoparticles which do not form agglomerates. 'Agglomerating' in this context means that several individual nanoparticles form agglomerates or clusters of nanoparticles. "Agglomerates" refer to agglomerated nanoparticles or clusters of nanoparticles.

The essential step of the present invention is the incubation/reaction with alkoxysilanes essentially in the absence of an organic solvent. "Essentially in the absence" in the context of organic solvents means that small traces of organic solvents may be present, preferably the amount of organic solvents is smaller than 10% by volume, more preferably smaller than 5% by volume, more preferably smaller than 1% by volume, especially smaller than 0.5% by volume. For example, minor amounts of methanol may be produced during the reaction and, therefore, to some extent may remain in the product. In a preferred embodiment, the coating is carried out in absence of an organic solvent, especially the coating is carried out in the absence of an added organic solvent. The preferred solvent for the coating reaction is water. Without being bound to any scientific theory, the inventors assume that these reaction conditions lead to a defined, however incomplete condensation reaction of the alkoxysilanes which translates into the agglomeration properties of the nanoparticles.

The method of the present invention is preferably carried out in the absence of ethylene glycol. Ethylene glycol interferes with the coating reaction of this invention. Furthermore, it is at least very difficult if not impossible to remove it completely from the nanoparticle preparation, as usually relatively large amounts of ethylene glycol remain attached to the coating of the nanoparticles and due to its high boiling point of 197° C. This applies also to the preparations prepared according to Lesniak et al. (1997, supra). According to the European Pharmacopeia only 600 ppm of ethylene glycol are allowed in the final medical product, which makes nanoparticle preparations with higher amounts of ethylene glycol inacceptable for commercial clinical use.

In one embodiment, the metal nanoparticles comprise iron, iron complex compounds, iron carbonyl compounds or iron salts, whereas iron salts are preferred. Iron comprising nanoparticles are preferred due to their low toxicity compared to other magnetic metals such as cobalt or nickel. In a preferred embodiment the iron complex compound, the iron carbonyl compounds or iron salts are essentially free of other metals and other contaminants in order to avoid toxicities. It is well known in the art that chemicals may contain traces of contaminants. Therefore, "essentially free" in this context means preferably that less than 1% by weight, preferably, less than 0.1% by weight of other contaminants is comprised within the iron complex compounds, iron carbonyl compounds or iron salts. Especially preferred are iron salts essentially free of other contaminants In an especially preferred embodiment, the iron salt is an iron oxide, preferably magnetite and/or maghemite. Such iron nanoparticles made of iron oxide can be manufactured by precipitating a solution containing a mixture of iron(III) chloride and iron(II) chloride with sodium hydroxide. "Iron nanoparticles" according to this invention are nanoparticles containing Fe atoms or Fe ions.

Accordingly, in a preferred embodiment, the aqueous suspension of iron oxide nanoparticles is provided by precipitating a solution containing a mixture of iron(III) chloride and iron(II) chloride with sodium hydroxide.

Here, the ratio between iron(III) chloride and iron(II) chloride is preferably of about 2:1.

In the context of the present invention, the terms "iron nanoparticles" and "iron oxide nanoparticles" are equivalently used.

Suitable precipitation reactions and conditions have been described by Massart (1981) and reviewed by Mohapatra and Anand (2010). Preferred conditions for the precipitation reaction are (i) a ratio of Fe(III)chloride and Fe(II)chloride of about 2:1; (ii) pouring the Fe(III)chloride and Fe(II)chloride solution into a sodium hydroxide solution with a concentration of about 2.13 M; (iii) precipitation temperature of about 25° C.; and (iv) time for the precipitation reaction of about 52 min. Optionally, the sodium hydroxide solution is poured into the iron chloride solution (instead of vice e versa) during a period of about 39 min at about 15° C. A method for producing coated iron oxide nanoparticles by means of precipitating iron salts in solution is, for example, exemplified in Example 1.1.

Alternatively, the aqueous suspension of iron oxide nanoparticles can be provided by thermal decomposition of an iron salt or an iron complex compound. The term "iron complex compound" as used herein generally means any complex containing iron, preferably any compound comprising complexed iron. Suitable methods have been described by Waldoefner and Stief (2011). Briefly, an iron-containing compound and an organic solvent are kept for 10 min at a temperature between 50° C. and 50° C. below the reaction temperature. Next, the solution is heated to 200 to 400° C. to yield nanoparticles. The nanoparticles are oxidized with oxygen, peroxide or a tertiary amineoxide, and treated with nitric acid and ironnitrate resulting in maghemite nanoparticles. Another suitable method for the preparation of iron oxide nanoparticles by thermal decomposition has been described by Guardia et al. (Guardia et al. 2010 a; Guardia et al. 2010 b; Guardia et al. 2012). Briefly, iron (III) acetylacetonate is mixed with decanoic acid in dibenzyl ether. The solution is constantly heated up to 200° C. After 2 h at 200° C. the solution is heated up to reflux and kept at this temperature for 1 h and finally cooled down to room temperature, washed and collected by centrifugation. Both methods are preferred due the high SAR of the resulting nanoparticles. A method for producing iron oxide nanoparticles by means of thermal decomposition according to the present invention is, for example, described in Example 1.2.

Accordingly, in an alternatively preferred embodiment, the aqueous suspension of iron oxide nanoparticles is provided by thermal decomposition of an iron salt or an iron complex compound.

Iron salts and iron complexes which are applicable in the method of the present invention are well known to the person skilled in the art and include, but are not limited to, iron(III) chloride, iron(II) chloride, iron (III) acetylacetonate, iron carbonyls and equivalents.

In a preferred embodiment, the metal nanoparticles are treated with $H_2O_2$ prior to the incubation/reaction with alkoxysilane. This optional step is preferred as the iron is fully oxidized to $Fe_2O_3$ (maghemite) under defined conditions and, as a consequence, subsequent reaction steps can be conducted in the absence of a protective gas (e.g. argon). Otherwise in the absence of $H_2O_2$, it is preferred to work under protective gas such as argon in order to control reaction conditions.

The alkoxysilan is preferably a trialkoxysilane. It is preferably selected from the group consisting of 3-(2-aminoethylamino)-propyl-trimethoxysilane (DIAMO), 3-aminopropyltriethoxysilane (APTES), trimethoxysilylpropyl-diethylenetriamine (TRIAMO) and N-(6-aminohexyl)-3-aminopropyl-trimethoxysilane. In an especially preferred embodiment, the alkoxysilane is 3-(2-aminoethyl-amino)-propyl-trimethoxysilane.

In a further preferred embodiment, the coating reaction is carried out by adding 0.3 to $0.6 \times 10^{-3}$ mol, preferably 0.4 to $0.5 \times 10^{-3}$ mol and especially 0.43 to $0.45 \times 10^{-3}$ mol trialkoxysilane per 0.9 mol of the metal.

According to a preferred embodiment of the invention, the incubation/reaction with alkoxysilane is performed at a pH of between 2 and 6 (which means that also a pH of 2 or 6 is included into this range), preferably of between 2.5 and 5.5, especially of 4.5±1. During the incubation/reaction, the pH may be adjusted to said values, if required. Acetic acid can be used to adjust the pH accordingly.

Preferably, the metal magnetic nanoparticles are disintegrated prior to the incubation/reaction with alkoxysilane. The nanoparticles are disintegrated preferably by ultrasound treatment in order to generate a suspension of ball-shaped or cubic electron-dense nanoparticles which can then be subjected to the coating reaction. In one embodiment, ultrasound treatment is done in an ultrasonic bath at 45 kHz 30 min to 2 h, especially for about 1 h. This disintegration method preferably is carried out at acidic conditions, preferably between pH 2.5 and 3.0. Disintegration of nanoparticles according to the present invention is, for example, described in Example 1.1.

Another suitable method for disintegrating nanoparticles is laser-based deagglomeration/laser fragmentation technique (Schnoor et al. 2010).

The method of this invention may further comprise the step of disintegrating the agglomerates after starting the incubation/reaction with alkoxysilane, which can be carried out as described above. In one embodiment, disintegration of the nanoparticles starts with or after the coating step. However, in a further preferred embodiment the disintegration step starts prior to the coating step and is further carried out simultaneously with and/or after the coating step. Especially, disintegration is started prior the coating step and is continued during and after the coating step. Preferably, disintegration is carried out for a total of about 24 h or more.

Upon coating and disintegration, a suspension can be generated that can stably be stored at room temperature making it a preferred embodiment. Not bound to any scientific theory it is assumed that most individual nanoparticles are completely coated with the alkoxysilane, which easily adhere to neighboring nanoparticles and form the agglomerates according to this invention, as can be seen in FIG. 1. Still, the suspension is fluent enough to easily pass through syringes and to be injectable into tumor tissue.

In a preferred embodiment, an additional step for removing incompletely coated and/or very large agglomerates (e.g. agglomerates of more than 2,000 nanoparticles) from the suspension is carried out. Suitable methods for this step are centrifugation (e.g. for 10 min at 2,000 rpm) and filtration (e.g. through a pleated filter with a pore size of 12-25 µm). In an especially preferred embodiment, both centrifugation and filtration are carried out. It has been observed that predominantly and completely alkoxysilane-coated nanoparticles do not sediment from the suspension e.g. if centrifuged for 10 min at 2,000 rpm. Accordingly the supernatant of the centrifugation and/or the flow-through of the filtration is/are a suspension according to the invention which does/do not show sedimentation over one day, preferably one week, especially one month, and therefore can be stored over a long time.

On the other hand, incompletely coated nanoparticles can be removed to a large extent from the suspension e.g. by such centrifugation. Such removal of incompletely coated nanoparticles is preferred, as incompletely coated nanoparticle have a reduced SAR which therefore reduce the volume SAR of a suspension.

The disintegration step(s) and optionally the removal step is/are preferably carried out until the agglomerates of the metal nanoparticles have an average size (z-average) of 30 to 450 nm, preferably of 50 to 350 nm and especially of 70 to 300 nm as determined by light scattering. In this context the average size is determined in water according to example 3. With this light scattering measurement, the size of agglomerates of nanoparticles is determined—in contrast to the size of the ball-shaped or cubic electron-dense single nanoparticles which are forming such agglomerates. "Z-average" with respect to the size of agglomerates means the readout of the light scattering size determination as carried out in example 3. Z-average values above the provided ranges lead to sedimentation of the nanoparticles and are therefore generally not suitable for the foreseen applications of these nanoparticles. Even if the dispersion may be reconstituted prior to instillation of a tumor, larger agglomerates may lead to serious problems, as the dispersion may partially separate into buffer and agglomerates while passing through the needle leading to an uneven distribution of the nanoparticles within the tissue.

In another preferred embodiment of the invention, the suspension of agglomerates is concentrated to a concentration of at least about 2 M, preferably of at least about 3 M, more preferably of at least about 4 M, more preferably of at least about 5 M, and especially of at least about 6 M as determined by its metal content. The desired metal concentration within the suspension according to this invention can be adjusted by evaporating water in a rotation evaporator. Suspension samples can be analyzed regarding solids content and metal-concentration using the method disclosed below (see, for example, Example 2).

Surprisingly, it has been found that the nanoparticles in the composition according to this invention can be concentrated to high concentrations of 2 M of metal content and above, without losing their usability as medical device or medicament. These highly concentrated suspensions can still be infused or injected in the daily routine and, importantly, can be stored over months. After autoclaving of the suspension, some gelling can be observed, which, however, can be reversed by intense vortexing (e.g., for about 12 hours). Compared to a suspension with lower metal concentration, these suspensions have a higher specific absorption rate (SAR) based on volume and a high viscosity. Surprisingly, it was shown for the nanoparticles of the invention that the depot formation of such nanoparticles within the intended tissue, e.g. tumor, depends on the concentration of the nanoparticles, i.e. increasing nanoparticle concentrations lead to an improved depot formation. This result was unexpected, as one can reasonably assume that the concentration of injected nanoparticles is quickly equalized for different concentrations within the tissue, so that identical nanoparticles in different concentrations do not behave differently.

Another aspect of the present invention is a suspension of agglomerates of magnetic alkoxysilan-coated metal nanoparticles obtainable by a method described above. As shown in the examples below this suspension can be injected in the daily routine into tumors, remains within the tumor tissue and therefore can be used for hyperthermia and thermoablation. It has surprisingly been found that the alkoxysilane-coating according to this invention leads to the properties of the nanoparticles to agglomerate in such a way that upon injection into tissue the agglomerates mostly stay in close proximity of the injection site but still are easy to handle. This makes these agglomerates especially suitable for the injection into tumor tissues e.g. for hyperthermia and/or thermoablation.

A further aspect of the invention is a composition comprising agglomerates of magnetic alkoxysilane-coated metal nanoparticles, wherein the agglomerates have an average size of 30 to 450 nm, preferably of 50 to 350 nm and especially of 70 to 300 nm as determined by light scattering. The size measurement of agglomerated nanoparticles according to the present invention is, for example, described in Example 3.

Preferably, this composition comprising agglomerates is essentially free of organic solvents. "Essentially free of organic solvents" in this context means that the small traces of organic solvents may be present, e.g. the amount of organic solvents is smaller than 5% by volume, preferably 1% by volume, more preferably smaller than 0.5% by volume, especially smaller than 0.1% by volume. In an especially preferred embodiment, no organic solvent can be detected in the nanoparticle preparation by customary methods.

The metal nanoparticles of such compositions are preferably nanoparticles having a metal core with a size of 5 to 25 nm, preferably with a size of 7 to 20 nm and especially with a size of 9 to 15 nm as determined by electron microscopy. The agglomerates of the suspension are preferably composed of dozens to hundreds of such individual nanoparticles, whereas any or only very few are small agglomerates of less than ten nanoparticles as determined in transmission electron microscopy (TEM) preferably less than 3 agglomerates of 10 or less nanoparticles in a representative TEM picture displaying 700 by 700 nm and at least 1000 nanoparticles. Transmission electron microscopy according to the present invention is, for example, described in Example 6.

In turn, in a representative TEM picture displaying 700 by 700 nm and at least 1000 nanoparticles less than 10 individual nanoparticles, preferably less than 5 individual nanoparticles, especially one or none individual nanoparticle can be detected. A nanoparticle in this context is one basically ball-shaped or cubic electron-dense nanoparticle visible in transmission electron micrographs. A single nanoparticle is a nanoparticle which is not attached to at least one other nanoparticle.

Preferably, the shape of the single nanoparticles is ball-shaped or cubic. Size and shape of the nanoparticles can be tailored by adjusting pH, ionic strength, temperature, nature of the salts (perchlorates, chlorides, sulfates, and nitrates), or the Fe(II)/Fe(III) concentration ratio (reviewed by Mohapatra and Anand 2010).

Preferably, the metal nanoparticles comprise iron, iron complex compounds, iron carbonyl compounds or iron salts, preferably iron salts. The iron salt is preferably an iron oxide, especially magnetite. The preferred nanoparticles can be obtained by the methods as described above, preferably by providing the suspension of iron oxide nanoparticles by precipitating a solution containing a mixture of iron(III) chloride and iron(II) chloride with sodium hydroxide.

In a preferred embodiment, the composition comprising agglomerates of magnetic alkoxysilane-coated metal nanoparticles of the invention have a zeta potential of 25 to 80 mV, preferably of 35 to 70 mV, especially of 45 to 60 mV. The zeta potential of the composition is determined as described in Example 4 at pH 5.2 and at a conductivity of 2.0 mS/cm (each determined at 25° C.). The zeta potential is dependent on the successful coating of the nanoparticles as it depends on the amino groups of the alkoxysilanes. Lower zeta potentials indicate an insufficient coating of the nanoparticles. The correct zeta potential within the provided ranges contributes to the properties of the nanoparticles upon injection into tissue, i.e. that injected nanoparticles remain at or near the injection site within, for example, the tumor, and do not spread to surrounding tissue, which would limit the applicable magnetic field and thereby the success of the treatment. Furthermore, the zeta potential in the provided ranges ensures optimal colloidal stability and therefore extends the shelf life of the nanoparticle composition.

A further preferred embodiment of this invention is a composition comprising agglomerates of magnetic alkoxysilane-coated metal nanoparticles, wherein the agglomerates are suspended in a water-based physiologically acceptable buffer. Physiologically acceptable buffers are known in the art and include for example acetate, citrate, carbonate or phosphate at an pH (at 25° C.) between 5 and 8, preferably between 5 and 6, and especially between 5.1 and 5.8 and a conductivity (at 25° C.) of 1.5 to 2.5 mS/cm, preferably 1.7 to 2.3 mS/cm. The osmolality of a suitable suspension is 0.01 to 0.05 Osmol/kg, preferably 0.02 to 0.04 Osmol/kg. Such suspensions are preferably ready to use as infusions for systemic treatment or injections for interstitial or intratumoral application.

The composition of this invention preferably has a nanoparticle concentration of at least about 2 M, preferably of at least about 3 M, more preferably of at least about 4 M, more preferably of at least about 5 M and especially of at least about 6 M, as determined by its metal content. Preferably, the nanoparticle concentration is below about 8 M, as too high concentrations, for certain applications, may lead to difficulties during injection due to the high viscosity of the dispersion. With respect to iron 2 M equals 112 mg/ml. The concentration of metal can be determined by photometry certain metal complexes, e.g. iron can be determined after transformation into an iron(II) phenanthroline complex as described in Example 2.

Surprisingly, it has been found that the nanoparticles in the composition according to this invention can be concentrated to high concentrations of 2 M of metal content and above, without losing their usability as medical device or medicament. These highly concentrated suspensions can still be infused or injected in the daily routine and, importantly, can be stored over months. After autoclaving of the suspension some gelling can be observed, which however can be reversed by intense vortexing (e.g. 12 hours). Compared to a suspension with lower metal concentration, these suspensions have a higher SAR based on volume and a high viscosity. Surprisingly, it was shown for the nanoparticles of the invention that the depot formation of such nanoparticles within the intended tissue, e.g. tumor, depends on the concentration of the nanoparticles, i.e. increasing nanoparticle concentrations lead to an improved depot formation. This result was unexpected, as one can reasonably assume that the concentration of injected nanoparticles is quickly equalized for different concentrations within the tissue, so that identical nanoparticles in different concentrations do not behave differently.

As can be seen in Example 9, more nanoparticles could be deposited within the tumor for highly concentrated compositions (e.g. 95% of injected iron for a 6 M suspension versus 90% for a 2 M suspension at day 0). This finding is consistent with the results that less iron was found in lung, liver and spleen for the 6 M suspension compared to 2 M suspension (e.g. 3% versus 14% at day 0). Accordingly, it is concluded that the higher the concentration the less nanoparticles enter the circulation and end up in other organs.

Furthermore, it was found that higher concentrated nanoparticles of the invention completely remain within the tumor within a time frame of 7 days (for 6 M suspension: 95% at day 0 versus 96% at day 7), whereas some losses of iron content can be observed over the same time frame for a lower concentrated suspension (2 M suspension: 90% at day 0 versus 86% at day 7). This finding is especially surprising as one would expect that nanoparticles are quickly diluted upon injection into the tumor tissue and do not show different behavior over longer time periods.

The composition of this invention preferably has a viscosity at a shear rate of 100/s of equal or more than 0.005 Pa s, preferably equal or more than 0.01 Pa s, more preferably equal or more than 0.1 Pa s, and especially equal or more than 1 Pa s, as determined by rotational rheometry. Rotational rheometry according to the present invention is, for example, exemplified in Example 8. Viscosity increases for suspensions according to this invention with increasing nanoparticle or iron concentration.

In a preferred embodiment, the specific absorption rate (SAR) of the nanoparticles within the composition of the invention is larger or equal than 2 W/g of the respective metal (e.g. iron), preferably larger or equal than 3 W/g of the respective metal and especially 4 to 50 W/g of the respective metal as determined at a magnetic field strength of 3.5 kA/m and a frequency of 100 kHz according to the method as described by Jordan et al. (1993). Generally, high SAR values are preferred, as consequently higher temperatures can be achieved during exposure to an alternating magnetic field. If the SAR value of the nanoparticles is too low, i.e. lower than the provided numbers, it is likely that upon exposure to an alternating magnetic field achieved temperatures throughout the tumor are too low to reach a therapeutic effect.

A further preferred embodiment of the invention is a composition according to this invention, wherein upon injection of the composition into an isogenic tumor model at or after day 7 after the injection at least 90%, preferably at least 93%, more preferably at least 95%, and especially at least 98% of applied metal remains within the injected tumor. An isogenic tumor model according to this invention is a tumor model, where the tumor cells, which are used to induce a tumor, are genetically matched to the host animal. For example, the C3H RS1 mammary carcinoma cell line is used to generate tumors in mice of strain C3H—HeN. Remaining metal in the tumor can be determined by measuring metal recovery using spectrometry, e.g. by a Tecan Infinite M 200 spectrometer.

A further embodiment of the invention is a composition which is obtainable by any of the methods of the invention.

A further aspect of the invention is a medical device comprising a suspension or a composition according to this invention. As the magnetic nanoparticles exert their therapeutic effect upon exposure to an alternating magnetic field through generation of heat as a physical mode of action and do not directly interact with the metabolism of the patient, these nanoparticles are classified in multiple jurisdictions as medical devices. Still, they can be used as powerful tools for the treatment or prophylaxis of tumor diseases and other diseases through hyperthermia and/or thermoablation, where cells are malfunctioning in a certain region of the body.

Examples for such other diseases which can be treated according to this invention are rheumatism, arthritis, arthrosis and bacterial infections. Tumor diseases which can be treated with the nanoparticles according to the invention are preferably solid tumors, especially local or locally advanced tumors or systemic tumor diseases which cause local problems such as inoperable metastasis. Examples are brain tumors, e.g. glioblastoma and astrocytoma, brain metastasis, prostate cancer, prancreatic cancer, hepatocellular carcinoma, head and neck cancer, bladder cancer, gastric cancer, renal cell carcinoma, ovarian carcinoma, cervical carcinoma, sarcoma, basal cell carcinoma and melanoma.

A further aspect of the invention is a medicament comprising a suspension or a composition according to this invention. The suspension or composition of the invention can be formulated with active pharmaceuticals such as anti-cancer agents, e.g. chemotherapeutic agents (which can be grouped into alkylating agents, antineoplastic antibiotics, anti-metabolites, natural source derivatives), hormones/growth factors or hormone/growth factor analogues or inhibitors, signal transduction inhibitors and immune therapeutics. Suitable pharmaceuticals are listed for example in Waldoefner and Stief (2011, paragraphs [0096] to [0102]). Accordingly, it is one aspect of the invention that the nanoparticles according to this invention are combined with such active pharmaceuticals.

In a further aspect, the present invention relates to a suspension or to a composition according to the present invention for use in a method of treating or preventing proliferative disease, cancer, tumors, rheumatism, arthritis, arthrosis and bacterial infections as further described above and below in a patient as defined above and below.

A further aspect of the invention is a method of treating or preventing proliferative disease, cancer, tumors, rheumatism, arthritis, arthrosis and bacterial infections comprising the step of administering the suspension or the composition of the invention to a human or animal patient as further described above and below.

Preferably, the suspension or composition for use according to this invention or the method of treating or preventing diseases according to this invention further include exposing the patient to an alternating magnetic field. Usually, the alternating magnetic field is applied hours or days after injecting the suspension or composition into the target region, e.g. tumor, of the patient (Johannsen et al. 2007; Thiesen and Jordan 2008; Maier-Hauff et al. 2011).

In analogy to Jordan et al. (2008) the suspension or compositions of this invention can further be used in a method for increasing the activity of an anti-cancer agent comprising the steps of administering to a patient in need thereof a pharmaceutical composition comprising the nanoparticle agglomerates as described herein and in a separate step administering at least one anti-cancer agent together with at least one pharmaceutically acceptable excipient, carrier and/or solvent. The two administrations may be simultaneously or one after the other (first nanoparticles, second anti-cancer agent or vice e versa), however in such a way that nanoparticles and anti-cancer agent are present at the same time within the patient's body in order to be able to act together and enhance each other's therapeutic effect. Whereas, according to this invention, the nanoparticle agglomerates remain within the tissue for months or years within the target area and can generate heat upon exposure to an alternating magnetic field, an administered anti-cancer agent typically acts for hours or days. "act together" in this context therefore means, that still sufficient pharmacologically active levels of the anti-cancer agent are present in the tissue. Accordingly, one further aspect of the invention are nanoparticles of the present invention for use in a method for the prophylaxis and/or treatment of tumor diseases, wherein the nanoparticles are administered together with anti-cancer agents in such a way, that nanoparticles and anti-cancer agent are present at the same time within the patient's body.

In a preferred embodiment the agglomerates of nanoparticles according to this invention are complexed with or covalently coupled to an active pharmaceutical agent or to a targeting agent such as antibodies, antibody fragments or ligands as known in the art. For example, the coupling of active pharmaceuticals and/or ligands to nanoparticles is described in Jordan et al. (2008), Gao et al. (2011), Waldoefner and Stief (2011) and Ivkov et al. (2005).

Other suitable pharmaceutical or medical device forms of the agglomerates of nanoparticles according to this invention than suspensions are powders, e.g. for inhalation or lyophilisates, which can be reconstituted prior to the infusion or injection, or implants comprising agglomerates of nanoparticles according to this invention, e.g. solid or gel-like medical devices, sponges or films as for example further described in Jordan (2009).

Generally, medicaments or medical devices according to this invention can easily be combined with conventional therapies used for the respective treatment or prophylaxis of the disease, such as chemotherapy or radiation. They can be used either to increase the effectiveness of the individual treatment and/or reduce side effects of the conventional therapy by lower their dose if combined with the medicaments or medical devices of this invention.

In light of the foregoing general discussion, the specific figures and examples presented below are illustrative only and are not intended to limit the scope of the invention. Other generic and specific configurations will be apparent to those persons skilled in the art.

FIGURES

FIG. 1: Transmission electron micrograph of a 2 M suspension of magnetic iron oxide nanoparticles manufactured according to Example 1.

Figure 2:
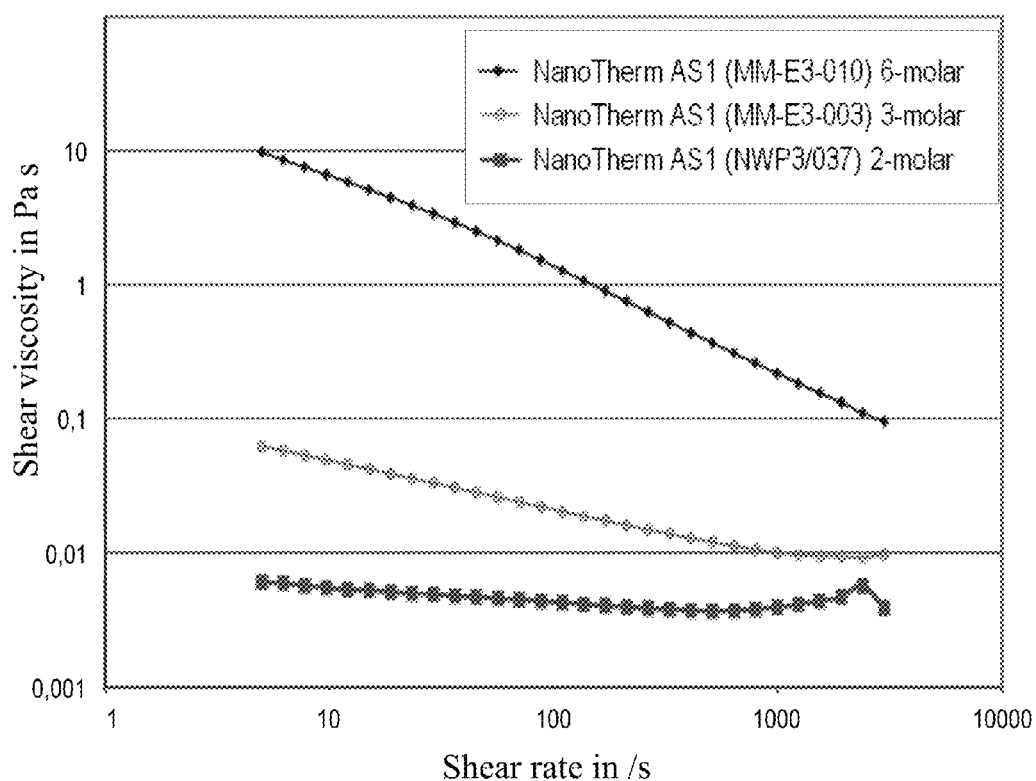

FIG. 2: The viscosity of three different iron-oxide nanoparticle preparations according to Example 1 has been determined by rotational rheometry according to Example 8. The shear viscosity in Pa s is depicted in dependence of the shear rate in /s for AS1(6 M Fe) [filled diamonds], AS2(3 M Fe) [open circles], and AS1(2 M Fe) [filled squares].

Figure 3:
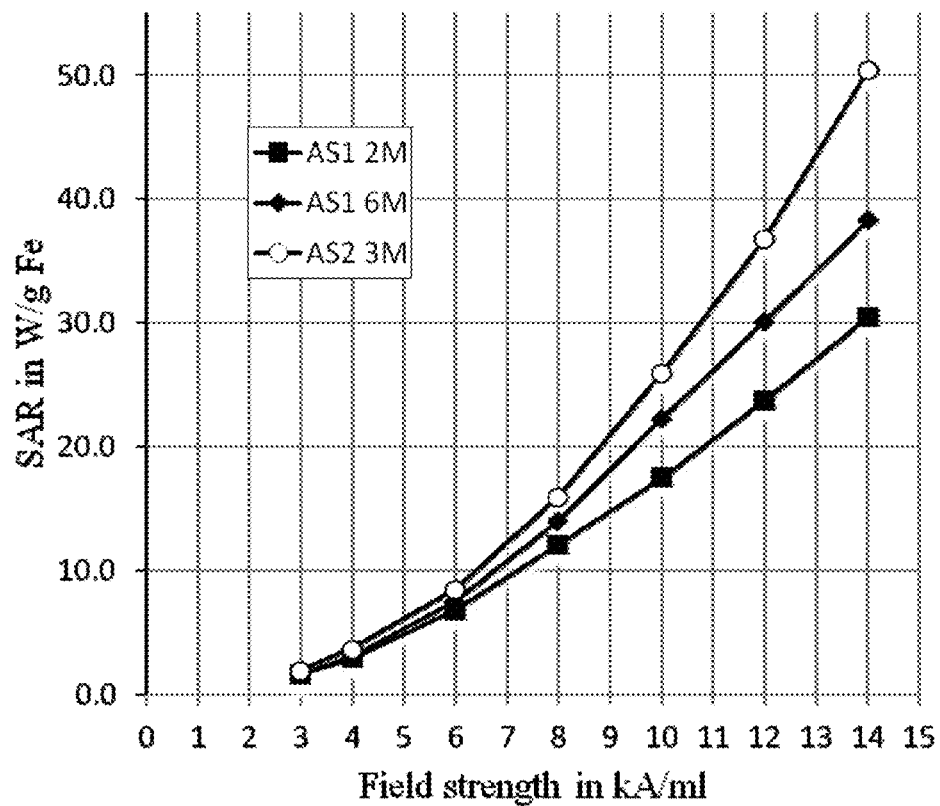

FIG. 3: The SAR of three different nanoparticle preparations according to Example 1 has been determined according to Example 5. The SAR in W/g Fe is depicted in dependence of the alternating magnetic field strength in kA/m for AS1(6 M Fe) [filled diamonds], AS2(3 M Fe) [open circles], and AS1(2 M Fe) [filled squares].

EXAMPLES

1. Manufacturing of Coated Magnetic Iron Oxide Nanoparticles 1.1. By Means of Precipitating Iron Oxide from Iron Salt Solutions (AS1 and AS2)

Precipitation and Washing: NaOH is weighted out into a flask, is solved in purified water to a concentration of 2.13 M and is subsequently chilled to 25° C. Fe(III)chloride and Fe(II)chloride (ratio 2:1) are filled into a glass bottle and solved in purified water to get a 0.48 M Fe(III)chloride/0.24 M Fe(II)chloride solution. The iron chloride solution is poured into the NaOH solution and is mixed during a period of about 53 min, while the temperature is constantly held at 25° C. The generated nanoparticles are left to sediment and the supernatant is removed. The nanoparticles are washed with degassed water until the supernatant reaches a conductivity of <5 mS/cm.

Optionally, the NaOH solution is poured into the iron chloride solution (instead of vice e versa) during a period of about 39 min at 15° C. This modification of the process has been performed for the AS2 nanoparticles.

Coating and Disintegration

The nanoparticle suspension from above is adjusted with diluted HCl until pH is between 2.5 and 3.0. Afterwards the flask is positioned in an ultrasonic bath and treated with ultrasound at 45 kHz for 1 h while stirring. Now over a time of 90 min 3-(2-aminoethylamino)-propyl)trimethoxysilane (Fluka, 48 ml per 1,2 l nanoparticle suspension) is added dropwise, while the pH is kept below a threshold of 5.5 by adding drops of acidic acid, but the pH shall not get lower than 5.0. After this step, the pH is adjusted to 4.65 with diluted HCl and the suspension is further treated with ultrasound for 23 hours. Particles manufactured according to this protocol (without the optional steps) are referred to as AS1 nanoparticles.

Optionally, the nanoparticles are treated with $H_2O_2$ for two days prior to the coating in order to achieve a finer dispersion of the nanoparticles and a better colloidal stability. Further $H_2O_2$ may be used in order to completely oxidize Fe under controlled conditions to $Fe_2O_3$. As a result subsequent reactions can be performed in the absence of a protections gas (e.g. argon). This optional step has been performed for the AS2 nanoparticles from above.

Dialysis: The suspension is purified with a blood dialysis cartridge (Fresenius F8 HPS) against degassed ultrapure water until a conductivity of 400 µS/cm is reached.

Centrifugation and Concentration: One half of the resulting suspension is filled in a centrifuge bucket and centrifuged for 10 min at 2,000 rpm. Next the supernatant is filtered through a pleated filter (12-25 µm) into a glass bottle, which has previously been rinsed for 5 min with Argon. This procedure is repeated identically with the second of the suspension. Afterwards, the nanoparticle suspension is concentrated with a rotation evaporator to the desired Fe concentration (e.g. 112 mg/ml Fe equals 2 M Fe, 168 mg/ml Fe equal 3 M Fe, or 335 mg/ml Fe equal 6 M Fe). Nanoparticle samples can be analyzed regarding solids content and Fe-concentration.

1.2. By Means of Thermal Decomposition of Iron Complex (AS4 and AS5)

AS4 particles were produced similar to the methods described in Waldoefner and Stief (2011). Briefly, iron(III) chloride sodium acetate, Diaminohexane and Ethyleneglycole were combined in a three necked flask and stirred until a homogeneous solution was obtained. Then the mixture was heated strongly until near boiling, and was refluxed for five hours. After washing and collecting the particles via centrifugation the dried particles were mixed with trimethyleneoxide in ethylene glycol and heated to 130° C. and kept for 2 h. Then the mixture was heated under reflux for 1 h. For the following oxidation step the washed particles were resuspended in nitric acid and treated with iron nitride. Then, after washing and collecting after the particles by centrifugation, the particles were coated with a tetraalkoxysilane in order to form a thick $SiO_2$-shell. Resulting particles were collected by centrifugation and resuspended in water. The final coating, disintegration and purification (dialysis, centrifugation and concentration) can be done in the same way as disclosed above for the AS1-particles.

AS5 particles were produced similar to the methods described by Guardia et al. (Guardia et al. 2010a; Guardia et al. 2010b; Guardia et al. 2012).

A solution of iron(III) acetylacetonate and decanoic acid in dibenzyl ether were rapidly heated up to 200° C. under stirring. Then the mixture was stirred for 2 h at this temperature and heated within 15 min to 298° C. This temperature was held for another hour. Finally the suspension was allowed to cool down to room temperature.

Then, acetone was added to the mixture and the precipitate was air-dried. The particles were resuspended in water. The final coating, disintegration and purification can be done in the same way as disclosed above for the AS1-particles.

2. Iron Concentration/Solids Content Determination

Determination of the iron concentration within a suspension is based on the photometric measurement of the extinction of an iron(II) phenanthroline complex. The complex is generated by extraction of the nanoparticles with hydrochloric acid until the extraction is complete as determined by visual inspection. All iron contained is reduced to iron (II) using hydroxylamine-hydrochloride and transformed into the phenanthroline complex in acetic acid/acetate buffer. Extinction of the complex is determined at 513 nm using a Shimadzu UV-1700 Pharmaspec against an iron(II) ethylendiammonium sulfate standard (Merck, Darmstadt).

The solids content of a suspension is determined by weighing e.g. 1 ml of the suspension prior to and after evaporation of the solvent (e.g. water).

3. Particle Size Measurement

To measure the average size of the nanoparticles a light scattering procedure is used to determine the hydrodynamic size of the nanoparticle preparation (e.g. Malvern ZetaSizer 3000 HSA or Malvern Zetasizer Nano ZS). The primary parameter is the z-average value, which is weighted by the scattering intensity. Therefore, in case of a polydisperse distribution, larger nanoparticles are weighted stronger than smaller ones. Furthermore, this method determines the average size of the nanoparticle agglomerates, and not the size of the single or primary nanoparticles.

Principle: If the nanoparticles or molecules are illuminated with a laser, the intensity of the scattered light fluctuates at a rate that is dependent upon the size of the nanoparticle/agglomerates as smaller nanoparticles are "kicked" further by the solvent molecules and move more rapidly. Analysis of these intensity fluctuations yields the velocity of the Brownian motion and hence the nanoparticle size using the Stokes-Einstein relationship.

Procedure: A small part of the test substance is diluted dependent on its concentration (1:1000 up to 1:3000). A sample of the diluted suspension is placed in the measurement device and treated according to recommendations of the Malvern ZetaSizer 3000 HSA.

4. Zeta Potential Measurement

To measure the Zeta potential of the nanoparticles, a sample is vortexed for 30 sec. 75 ml of a 1:1000 dilution of the solution with a concentration of about 0.11 mg/ml for Fe (or other metal) in ultrapure water is prepared and treated for 15 min with ultrasound. 20 ml of the solution are injected in the measuring cell of the Malvern ZetaSizer 3000 HSA (or Malvern Zetasizer Nano ZS) and measured according to the recommendations of the manufacture. The pH of the solution is determined with a separate pH meter.

5. SAR Measurement

The SAR of samples from Example 1 was determined according to the method developed by Jordan et al. (1993) at a frequency of 100 kHz and a field strength of up to 3.5 kA/m. Results for 3.5 kA/m and higher field strengths are shown in Table 1.

TABLE 1

Specific absorption rate

| | field strength in W/g at 100 kHz | SAR |
| --- | --- | --- |
| AS1 112 mg/ml Fe | 3.5 | 3.5 |
| AS1 112 mg/ml Fe | 7.5 | 9.45 |
| AS2 168 mg/ml Fe | 3.5 | 4.0 |
| AS2 168 mg/ml Fe | 6.0 | 8.56 |
| AS1 335 mg/ml Fe | 6.0 | 7.22 |
| AS4 112 mg/ml Fe | 3.0 | 4.02 |
| AS4 112 mg/ml Fe | 4.0 | 15.69 |
| AS5 112 mg/ml Fe | 6.0 | 11.99 |

SAR averages from several manufacturing runs of AS1 and AS2 nanoparticles at different alternating magnetic field strengths are shown in FIG. 3.

6. Transmission Electron Microscopy

Electron microscopy of nanoparticles can be done by TEM analysis in analogy to the method described by Jordan et al. (1996, page 712, 3.2.2).

A 2 M suspension of magnetic iron oxide nanoparticles manufactured according to Example 1 has been analyzed by TEM. The resulting micrograph is shown as FIG. 1. On the micrograph, large agglomerates of nanoparticles (a single nanoparticle is pointed to by an arrow) can be seen. No individual nanoparticles can be observed within the depicted area—all nanoparticles are attached to others.

7. Suspension Specifications

One production run according to example 1 lead to the physical/chemical specifications as depicted in Table 2.

TABLE 2

Specifications of a representative charge

| | AS1 | AS4 | AS5 |
|---|---|---|---|
| particle size (z-average) | 89 nm | 179.6 | 180.8 nm |
| zeta potential | 53.5 mV | 47.8 mV | 42.5 mV |
| conductivity (25° C.) | 2.16 mS/cm | 0.90 mS/cm | — |
| pH (25° C.) | 5.28 | 4.38 | — |
| Osmolality | 0.03 Osmol/kg | 0.08 Osmol/kg | — |
| SAR (at 100 kHz, at given field strength) | 10 W/g Fe (7.5 kA/m) | 14 W/g Fe (4 kA/m) | 12 W/g Fe (6 kA/m) |
| total metal content (Fe) | 15% by weight | 18% by weight | — |
| concentration (Fe) | 1.99 mol/l | 1.70 mol/l | 1.88 mol/l |

8. Rotational Rheometry/Viscosity Measurement

The viscosity of the nanoparticle samples was determined by Malvern material characterization services using rotational rheometry at 20° C., wherein the shear viscosity (in Pa s) was determined in dependence of the shear rate (from 7 to 1500/s). Results for nanoparticle preparations according to Example 1 are shown in FIG. 2.

9. Depot Formation of Magnetic Fluids in vivo $1 \times 10^6$ tumor cells of the C3H RS1 mammary carcinoma cell line were injected in the right hind limb of mice of the strain C3H—HeN (Harlan Laboratories, Borchen). Once induced tumors had a volume of 0.57 to 0.85 cm³, animals were randomized (15 animals per group) and tumors of the right hind limb were injected with the magnetic fluid of Example 1 having an Fe concentration of either 112 or 335 mg/ml. The exact injection volume content was determined by weighing the injection syringe prior and after injection and calculating the difference (on average 31 µl±5.8 µl).

The total Fe content of tissue/tumor of the mice was determined after 0 or 7 days by UV-vis measurement at 565 nm using the Spektroquant 14761 test (Merck, Darmstadt) and a Cary 50 (Agilent Technologies, Santa Clara, Calif., USA) and a Tecan Infinite M 200 (Tecan Group Ltd, Mannedorf, Switzerland) spectrometer. The initially applied Fe content was determined by subtracting from the total Fe content of the tissue/tumor the initial content of the tissue (determined by measuring the Fe content of the non-inoculated left leg) and the loss of magnetic fluid during inoculation which was absorbed by the used swab. Fe recovery (average of 15 tumors per group) was calculated as the total Fe content divided by initially applied Fe content.

TABLE 3

Fe recovery as determined by Cary 50

| Cary | | Fe recovery tumor [%] | Fe recovery lung/liver/spleen [%] | Fe recovery tumor/lung/liver/spleen [%] |
|---|---|---|---|---|
| 112 mg/ml Fe | day 0 | 90 | 14 | 104 |
| | day 7 | 86 | 10 | 96 |

TABLE 3-continued

Fe recovery as determined by Cary 50

| Cary | | Fe recovery tumor [%] | Fe recovery lung/liver/spleen [%] | Fe recovery tumor/lung/liver/spleen [%] |
|---|---|---|---|---|
| 335 mg/ml Fe | day 0 | 95 | 3 | 98 |
| | day 7 | 96 | 3 | 99 |

TABLE 4

Fe recovery as determined by Tecan Infinite M 200

| Tecan | | Fe recovery tumor [%] | Fe recovery lung/liver/spleen [%] | Fe recovery tumor/lung/liver/spleen [%] |
|---|---|---|---|---|
| 112 mg/ml Fe | day 0 | 95 | 16 | 111 |
| | day 7 | 93 | 13 | 106 |
| 335 mg/ml Fe | day 0 | 98 | 4 | 102 |
| | day 7 | 98 | 4 | 102 |

Considering the initial Fe content (as determined in the left leg) and the losses due to the smaller inoculation volume of the magnetic fluids, recovery rates of total Fe on average for all four groups were 99% for Cary 50 and 104% for Tecan Infinite M 200. Generally, the recovery figures were higher using the Tecan Infinite M 200 (Table 4) versus Cary 50 (Table 3).

Comparing Fe recovery rates between the 112 mg/ml Fe formulation and the 335 mg/ml Fe formulation, both determinations revealed a tendency that at day 0 more Fe nanoparticles were retained within the tumor for the 335 mg/ml formulation (95% versus 90% as determined by Cary, and 98% versus 95% as determined by Tecan). On the other hand, amounts of Fe nanoparticles found in other tissues (lung, liver and spleen) at day 0 were much higher for the 112 mg/ml Fe formulation (14%/16% for 112 mg/ml versus 3%/3% for 335 mg/ml). Therefore, it can be concluded that more Fe nanoparticles are flushed out from the tumor during and potentially immediately after application within day 0 for the lower concentrated formulation compared to the higher concentrated formulation.

In order to determine the ratio of Fe that remains after 7 days within the tumor compared to Fe that effectively was applied to the tumor at day 0, Fe recovery rates at day 0 were divided by Fe recovery rates at day 7 and averaged between the determinations by the Cary 50 and Tecan Infinite M 200 (results shown in Table 5). Similarly, the fate of the Fe that accumulated at day 0 in lung, liver and spleen was analyzed by comparing the amount to the Fe still present within these organs at day 7.

TABLE 5

Remaining Fe within tumor/organs after 7 days (ratio between Day 0 and Day 7, averaged between Cary and Tecan)

| | Remaining Fe tumor [%] | Remaining Fe lung/liver/spleen [%] |
|---|---|---|
| 112 mg/ml Fe | 97% | 75% |
| 335 mg/ml Fe | 101% | 100% |

Whereas for the 112 mg/ml Fe formulation there was a further loss of about 3% Fe from day 0 to day 7, the Fe content for the 335 mg/ml Fe formulation stayed constant during this time frame. Interestingly, about ¼ of the Fe which found its way to the lung, liver and spleen for the 112 mg/ml Fe formulation disappeared within a week, whereas all of the Fe from the 335 mg/ml formulation found in these organs at day 0 remained there til day 7 (although one has to consider that total amounts of Fe found in these organs for the 335 mg/ml Fe formulation were in total only about ¼ of the amount Fe found in these organs for the 112 mg/ml Fe formulation, see Table 3 and Table 4, column "Fe recovery lung/liver/spleen").

Accordingly, the higher concentrated nanoparticle formulation additionally shows an improved retention rate of nanoparticles within the tumor over a 7 day period, which is of large importance, if patients are subjected to multiple treatments with a magnetic field over weeks or months.

LITERATURE

Gao, J., et al. (2011). WO 2011/082796.
Guardia, P., et al. (2012). ACS Nano 6(4): 3080-91.
Guardia, P., et al. (2010a). Chem Commun (Camb) 46(33): 6108-10.
Guardia, P., et al. (2010b). Langmuir 26(8): 5843-7.
Gupta, A. K. and M. Gupta (2005). Biomaterials. 26(18): 3995-4021.
Ivkov, R., et al. (2005). Therapy via Targeted Delivery of Nanoscale Particles. US 2005/0090732.
Johannsen, M., et al. (2007). Eur Urol. 52(6): 1653-61. Epub 2006 Nov. 17.
Jordan, A. (2009). Implantable Products comprising Nanoparticles. WO 2009/100716.
Jordan, A., et al. (2008). Nanoparticle/Active Ingredient Conjugates. US 2008/0268061.
Jordan, A., et al. (2008). Method of Carrying Therapeutic Substances into Cells. US 2008/0187595.
Jordan, A., et al. (1993). Int J Hyperthermia. 9(1): 51-68.
Jordan, A., et al. (1996). Int J Hyperthermia. 12(6): 705-22.
Lesniak, C., et al. (1997). U.S. Pat. No. 6,183,658.
Maier-Hauff, K., et al. (2011). J Neurooncol 103(2): 317-24.
Massart, R. (1981). IEEE Trans. Magn. 17(2): 1247-48.
Mohapatra, M. and S. Anand (2010). Int J of Engineering, Science and Technology. 2(8): 127-46.
Moroz, P., et al. (2002). Int J Hyperthermia. 18(4): 267-84.
Ruefenacht, D., et al. (2006). WO 2006/125452.
Schnoor, A., et al. (2010). Chemie Ingenieur Technik 82(3): 317-26.
Thiesen, B. and A. Jordan (2008). Int J Hyperthermia. 24(6): 467-74.
Waldoefner, N. and K. Stief (2011). Magnetic Transducers. US 2011/0052609.

The invention claimed is:

1. A method for producing a suspension of agglomerates of magnetic alkoxysilane-coated metal nanoparticles, wherein an aqueous suspension of magnetic metal nanoparticles is incubated with alkoxysilane, wherein said incubation is carried out in the absence of added organic solvent, wherein the alkoxysilane is trialkoxysilane and wherein 0.3 to $0.6 \times 10^{-3}$ mol trialkoxlysilane is added per 0.9 mol metal.

2. The method according to claim 1, wherein the metal nanoparticles comprise iron, iron complex compounds, iron carbonyl compounds or iron salts.

3. The method according to claim 2, wherein the iron salt is an iron oxide.

4. The method according to the claim 3, wherein the aqueous suspension of iron oxide nanoparticles is
   a) provided by precipitating a solution containing a mixture of iron (III) chloride and iron (II) chloride with sodium hydroxide, or
   b) provided by thermal decomposition of an iron salt or an iron complex compound.

5. The method according to claim 1, wherein the magnetic metal nanoparticles are treated with $H_2O_2$ prior to the incubation.

6. The method according to claim 1, wherein the trialkoxysilane is selected from the group consisting of 3-(2-aminoethylamino)-propyl-trimethoxysilane, 3-aminopropyltriethoxysilane, trimethoxysilylpropyl-diethylenetriamine and N-(6-aminohexyl)-3-aminopropyltrimethoxysilane.

7. The method according to claim 1, wherein 0.4 to $0.5 \times 10^{-3}$ mol trialkoxysilane is added per 0.9 mol metal.

8. Method according to claim 1, wherein the incubation is performed at a pH between 2 and 6.

9. Method according to claim 1, wherein the metal magnetic nanoparticles are disintegrated prior to the incubation with alkoxysilane.

10. Method according to claim 1, further comprising the step of disintegrating the magnetic nanoparticles after starting the incubation with alkoxysilane.

11. Method according to claim 1, further comprising the step of removing incompletely coated nanoparticles.

12. Method according to claim 9, wherein the agglomerates are disintegrated until an average size of 30 to 450 nm as determined by light scattering is achieved.

13. Method according to claim 1, wherein the suspension of agglomerates is concentrated to a concentration of at least about 2 M as determined by its metal content.

14. The method according to claim 1, wherein the suspension of agglomerates is concentrated to a concentration of at least about 6 M as determined by its metal content.

15. The method according to claim 3, wherein the iron salt is magnetite.

16. The method according to claim 3, wherein the iron salt is maghemite.

* * * * *